US006462028B2

(12) United States Patent
Pendergast et al.

(10) Patent No.: US 6,462,028 B2
(45) Date of Patent: Oct. 8, 2002

(54) METHOD OF PROMOTING CERVICAL AND VAGINAL SECRETIONS

(75) Inventors: William Pendergast, Durham, NC (US); Sammy R. Shaver, Chapel Hill, NC (US); David J. Drutz, Chapel Hill, NC (US); Janet L. Rideout, Raleigh, NC (US); Benjamin R. Yerxa, Raleigh, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 09/199,912

(22) Filed: Nov. 25, 1998

(65) Prior Publication Data

US 2002/0013289 A1 Jan. 31, 2002

Related U.S. Application Data

(63) Continuation-in-part of application No. 09/122,516, filed on Jul. 24, 1998, now Pat. No. 6,319,908.
(60) Provisional application No. 60/054,147, filed on Jul. 25, 1997.

(51) Int. Cl.$^7$ ................. C07H 19/10; C07H 19/20; C07H 19/207
(52) U.S. Cl. .............. 514/47; 514/48; 514/50
(58) Field of Search .............. 514/47, 48, 51

(56) References Cited

U.S. PATENT DOCUMENTS

| | | | |
|---|---|---|---|
| 3,639,561 A | 2/1972 | Gordon et al. | 424/28 |
| 3,639,562 A | 2/1972 | Gordon et al. | 424/28 |
| 5,635,160 A | 6/1997 | Stutts, III et al. | 424/45 |
| 5,763,447 A | 6/1998 | Jacobus et al. | 514/265 |
| 5,789,391 A | * 8/1998 | Jacobus et al. | 514/51 |
| 5,837,861 A | * 11/1998 | Pendergast et al. | 536/25.6 |
| 6,294,188 B1 | 9/2001 | Ragavan et al. | 424/433 |

FOREIGN PATENT DOCUMENTS

| | | |
|---|---|---|
| EP | 0566132 A | 10/1993 |
| WO | WO 96/40059 | 12/1996 |
| WO | WO 97/29756 | 8/1997 |
| WO | WO 97/35591 | 10/1997 |
| WO | WO 98/03177 | 1/1998 |
| WO | WO98/03182 | 1/1998 |
| WO | WO98/34593 | 8/1998 |
| WO | WO98/34942 | 8/1998 |
| WO | WO 99/05155 | 2/1999 |
| WO | WO 00/02552 | 1/2000 |
| WO | WO 00/30629 | 6/2000 |

OTHER PUBLICATIONS

Gorodeski, G.I., et al., "Regulation of the paracellular permeability of cultured human cervical epithelium by a nucleotide receptor," Journal of Thesociey for Gynecologic Investigation, vol. 2(5) 76–720 (1995).

Gorodeski, G., et al., "Purinergic Receptor–Induced Changes in Paracellular Resistanc eAcross Curltures of Human Cervical Cells Are Mediated by Two Distinct Cytosolic Calcium–Related Mechansims" *Cell Biochemistry and Biophysics*. 172:281–306 (1998).

Gorodeski, G., et al., "Retinoids modulate $P_{2u}$ purinergic receptor–mediated changes in transcervical paracellular permeability," *Am. Phy. Soc.* 274(Cell Physiol. 43):C1108–C1116 (1998).

Gorodeski, G., et al., "Retinoids regulate tight junctinal resistance of cultured human cervical cells," *Am. J. Pysiol.* 275(5 Pt. 1):C1707–C1713 (1997).

Gorodeski, G., et al., "Retinoids modulate P2Y2 nucleotide receptor mRNA in human uterine certical cells," *Am. J. Pysiol.* 275(3 Pt. 1):C758–C765 (1998).

Gorodeski, G., et al., "Exracellular ATP regulates transcervical permeabilityby modulating two distinct paracellular pathways," *Am. J. Pysiol.* 272(5 Pt. 1):C1602–C1610 (1998).

Gorodeski, G., "The cultured human cervical epithelium: a new model for studying paracellular transport," *J. Soc. Gynecol. Investing* 3(5):267–280 (1996).

Gorodeski, G., et al., "Nucleotide receptor–mediated decrease of tigh–junctional permeability to cultured human cervical epithelium," *Am. J. Pysiol.* 270(6 Pt. 1):C1715–C1725 (1996).

Gorodeski, G., et al., "Biphasic regulation of paracellular permeability in human cervical cells by two distinct nucleotide receptors," *Am. J. Pysiol.* 268(5 Pt. 1):C1215–1226 (1998).

Born, G.V. and Kratzer, M.A., "Source and conce tration of extracellular adenosine triphosphate during haemostasis in rats, rabbits and man," *J. Pysiol.* 354:419–429 (1984).

Bhadauria, S. et al., "Genital tract abnormalities and female sexual function impairment in systemic sclerosis" *Am. J. Obs. Gynecol.* 172:580–587 (1995).

Coste H., et al., "Non–adenylylated Bis(5'–nucleosidyl) Tetraphosphates Occur in *Saccharomyces cerevisiae* and in *Escherichia coli* and Accumulate upon Temperature Shift or Exposure to Cadmium*," *J. Biol. Chem.* 262(25):12096–12103 (1987).

(List continued on next page.)

Primary Examiner—James O. Wilson
Assistant Examiner—Howard Owens
(74) Attorney, Agent, or Firm—Albert P. Halluin; Viola T. Kung; Howrey, Simon, Arnold & White, LLP

(57) ABSTRACT

The present invention provides a method of stimulating cervical and vaginal secretions in a mammal by treatment with $P2Y_2$ and/or $P2Y_4$ purinergic receptor agonists. Treatment of vaginal dryness associated with menopause, chemotherapy, and various disease states as well as the treatment of vulvar pain is discussed. Suitable agonists such as UTP, CTP, ATP, dinucleotides and analogs thereof are disclosed.

8 Claims, No Drawings

OTHER PUBLICATIONS

Cust, M., et al., "Consequences and treatment of ovarian failure after total body irradiation for leukaemia" *Brit. Med. J. 299;*1494–1497 (1989).

Guranowski, A., et al., "Synthesis of Diadenosine 5',5'''–$P^1$, $P^4$–Tetraphosphate (AppppA) from Adenosine 5'–Phosphosulfate and Adenosine 5'–Triphosphate Catalyzed by Yeast AppppA Phosphorylase," *Biochemistry 27:*2959–2964 (1988).

Key, E. et al., "Management of vaginal dryness", *Clinical Gynaecology 5* (31):24–27 (1991).

Lobaton. C., et al., "Diguanosinetetraphosphatase from Rat Liver: Activity on Diadenosine Tretraphosphate and Inhibition by Adenosine Tetraphosphate," *Eur. J. Biochem. 50:*495–501 (1975).

Ng, E. and Orgel, L., "The action of a water–soluable carbodiimide and adenosine–5'–polyphosphates," *Nucleic Acid Res. 15*(8):3573–3580 (1987).

Rapaport, E., et al., "HeLa cell DNA polymerase α is tightly associated with tryptophanyl–tRNA synthetase and diadenosine 5',5'''–$P^1$,$P^4$–tetraphosphate binding activities," *Proc. Natl. Acad. Sci. 78*(2):838–842 (1981).

Reginald, W. et al., "Medroxyprogesterone acetate in the treatment of pelvic pain due to venous congestion" *Br. J. Obstet. Gynecol. 96:*1148–1152 (1989).

Sillero, M., et al., "Dinucleosidetriphosphatase from Rat Liver, Purification and Properties" *Eur. J. Biochem. 76:*331–337 (1977).

Sorokin, Y. et al., "Obstetric and Gynecologic Dysfunction in the Ehlers–Danlos Syndrome" *J. Reprod. Med 59:*281–284 (1994).

Sreenbny L. et al., "Xerostomia in Diabetes Mellitus" *Diabetes Care 15:*900–904 (1992).

Vallejo, C., et al., "Dinucleosidasetetraphosphatase in Rat Liver and *Artemia Salina,*" *Biochim. Biophy. Acta 438:*304–309 (1976).

Wisniewski, P. et al., "Postpartum vaginal atrophy" *Am. J. Obstet. Gynecol. 165:*1249–1254 (1991).

* cited by examiner

METHOD OF PROMOTING CERVICAL AND VAGINAL SECRETIONS

This application is a continuation-in-part of U.S. application Ser. No. 09/122,516 filed Jul. 24, 1998, which claims priority to U.S. Provisional Application Ser. No. 60/054,147, filed Jul. 25, 1997. Both applications are incorporated herein by reference.

TECHNICAL FIELD

This invention relates to a method of regulating secretions in and around the cervix and vagina of a patient by administering purinergic receptor agonists such as certain uridine, adenine, or cytidine triphosphates as well as other nucleoside phosphate containing compounds.

BACKGROUND OF THE INVENTION

Vaginal dryness is a very common problem which brings physical and emotional distress to many women (Key, E., *Nurs. Stand.* 5:24–27 (1991)). It most commonly manifests itself during sexual intercourse, which causes dyspareunia and can eventually lead to apareunia. Although it is traditionally considered to be a condition which affects postmenopausal women, it can occur during the premenopausal and perimenopausal years. The use of oral contraceptives may also cause a reduction in vaginal moisture in some women (Reginald, W., et al., *Br. J. Obstet. Gynaecol.* 96:1148–1152 (1989)). Postpartum vaginal dryness, independent of or as a result of lactation, can be a significant complaint (Wisniewski, P., et al., *Am. J Obstet. Gynecol.* 165:1249–1254 (1991)). Women undergoing chemotherapy or radiotherapy for malignant diseases such as leukemia often experience vaginal dryness as a result of treatment (Cust, M., et al., *Br. Med. J.* 299:1494–1497 (1989)). Many disease states, such as systemic sclerosis and other systemic autoimmune disorders (Bhadauria, S., et al., *Am. J. Obstet. Gynecol.* 172:580–587 (1995)), Ehlers-Danlos syndrome (Sorokin, Y., et al., *J. Reprod. Med.* 39:281–284 (1994)), diabetes mellitus (Sreebny, L., et al., *Diabetes Care* 15:900–904 (1992)), and Sjögren's syndrome (Marchesoni, D., et al., *Eur. J. Obstet. Gynecol. Reprod. Biol.* 63:49–53 (1995)) have decreased vaginal hydration and lubrication problems as significant disease-associated symptoms.

Vulvar pain is defined as the excessive sensitivity of the nerves supplying the mucus membrane of the vulva. This persistent burning and sensitivity in vulvar skin is not caused by identifiable infection. It cannot be cured by surgery. The diseases covered under "vulvar pain" are also referred to as vulvodynia/vulvar vestibulitis, vulvitis, burning vulvar syndrome and is often associated with fibromylagia, irritable bowel syndrome, Sjögren's syndrome, chronic inflammation, and Paget's disease as well as in the absence of any identifiable disease or infection. R. Paul St. Armad, M. D., an endocrinologist at UCLA, has successfully treated fibromylagia with uricosuric (gout) drugs, especially guaifenesin, a drug used to liquefy mucus (Yount, J. J. et al., *Women's Health Digest* 3(2) 1997). Dr. Armad has found that such gout drugs provide an effective treatment for fibromylagia, even though gout and fibromylagia have no connection. Dr. Armad has found that 24-hour urine samples taken from patients before and after treatment exhibited a significant increase in the excretion of phosphate and a moderate increase of oxalate and calcium after guaifenesin was started. His hypothesis is that an excess of intracellular phosphate, and possibly oxalate, builds up in the cells of fibromylagia sufferers and depresses formation of energy (ATP) in the mitochondria of the cells. It should be noted that the role of ATP in Dr. Armad's theory is as an energy source and not an agonist of the $P2Y_2$ receptor.

Current therapies for increasing vaginal moisture are: lubricating agents such as lubricating creams or jellies, topical estrogen creams, and HRT (hormone replacement therapy). Lubricating jellies provide short-lived and temporary relief, as these are aqueous preparations containing no pharmacologically active agent. Topical estrogen creams, if used on a regular basis, may be absorbed into the systemic circulation. This can cause endometrial stimulation and can lead to endometrial hyperplasia and carcinoma (Whitehead, M., et al., *N. Eng. J. Med.* 305:1599–1605 (1981)). HRT is effective at relieving symptoms of vaginal atrophy and hence vaginal dryness but has several contraindications and unwanted risks and side effects. A history of gall bladder disease (*N. Eng. J. Med.*, 290:15–19 (1974)) or a personal or family history of reproductive or breast cancer (Harlap, S., *Am. J. Obstet. Gynecol.* 166:1986–1992 (1992)) are contraindications for estrogen therapy. Other contraindications are: history of stroke, cardiovascular disease, deep-vein thrombosis, superficial thrombophlebitis, liver disease, heavy smoking, high blood pressure, diabetes, uterine bleeding or large fibroids, hyperlipidemia, and gross obesity (Lichtman, R., *J. Nurse Midwifery* 36:30–48 (1991)). One major disadvantage of HRT is the resumption of monthly withdrawal bleeds, which many postmenopausal women will not accept. Some women, even while on HRT, still experience a degree of vaginal dryness (Key, E., *Nurs. Stand.* 5:24–27 (1991)).

It has been shown that uridine 5'-triphosphate (UTP) and dinucleotides such as diuridine tetraphosphate are potent agonists of $P2Y_2$ purinergic receptors found on the surface of human airway epithelium. UTP has been shown to increase both the rate and total amount of mucin secreted by goblet cells in vitro (Lethem, M., et al., *Am. J. Respir. Cell Mol. Biol.* 9:315–322 (1993)). UTP has also been shown to increase chloride secretion, and hence, water secretion from airway epithelial cells in vitro (Mason, S., et al., *Br. J. Pharmacol.* 103:1649–1656 (1991)).

Thus, as a result of the ineffectiveness and risks of current therapies, medical researchers have sought to develop alternatives for the treatment of vaginal dryness. Because of the demonstrated ability of UTP and dinucleotides, such as diuridine tetraphosphate, to increase hydration of airway epithelial secretions and stimulate release of mucins, applicants were motivated to investigate whether UTP and other $P2Y_2$ and/or $P2Y_4$ purinergic receptor agonists could stimulate hydration and mucin production in the vaginal and cervical epithelia.

SUMMARY OF THE INVENTION

A method of stimulating cervical and vaginal secretions in a subject in need of such treatment is disclosed. The method of the present invention may be used to increase cervical and vaginal secretions for any reason, including, but not limited to, treatment of vaginal dryness and/or treatment of vulvar pain. Vaginal dryness is associated with but not limited to menopause, childbirth, breastfeeding, chemotherapy or radiotherapy, diabetes mellitus, Sjögren's syndrome, Ehlers-Danlos syndrome, systemic sclerosis and other systemic autoimmune diseases, hysterectomy, urogenital surgery, psychosomatic disorders, anxiety, psychosexual problems, and pharmacological drug-related side effects. The method of the present invention comprises administering a $P2Y_2$ and/or $P2Y_4$ purinergic receptor agonist: uridine 5'-triphosphate, $P^1,P^4$-di(uridine-5')tetraphosphate, cytidine 5'-triphosphate or adenosine 5'-triphosphate or analogs thereof, in an amount effective to stimulate vaginal and cervical secretions.

Another aspect of the present invention is the use of uridine 5'-triphosphate, $P^1,P^4$-di(uridine-5')tetraphosphate, cytidine 5'-triphosphate or adenosine 5'-triphosphate or analogs thereof, for the manufacture of a medicament for carrying out a therapeutic method of treatment as given above.

The present invention also discloses pharmaceutical compositions comprising uridine 5'-triphosphate, $P^1,P^4$-di(uridine-5')tetraphosphate, cytidine 5'-triphosphate or adenosine 5'-triphosphate or analogs thereof, with a pharmaceutical carrier therefor.

$X_1$, $X_2$ and $X_3$ are each independently either $O^-$ or $S^-$; preferably, $X_2$ and $X_3$ are $O^-$;

$R_1$ is O, imido, methylene or dihalomethylene (e.g., dichloromethylene or difluoromethylene); preferably, $R_1$ is oxygen or difluoromethylene;

$R_2$ is H or Br; preferably, $R_2$ is H; particularly preferred compounds of Formula I are uridine 5'-triphosphate (UTP) and uridine 5'-O-(3-thiotriphosphate) (UTPγS).

A dinucleotide is depicted by the general Formula II:

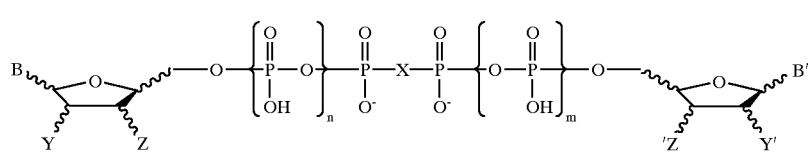

Formula II

DETAILED DESCRIPTION OF THE INVENTION

Applicants have discovered that uridine 5'-triphosphate (UTP) and related compounds are potent agonists for purinergic receptors found in cervical and vaginal epithelia preparations. The methods of the present invention are an improvement upon the current most commonly used treatments of vaginal dryness as UTP stimulates a patient's own production and secretion of mucins as well as increasing the levels of mucosal hydration, which serve to maintain the natural protective and lubricant characteristics of vaginal and cervical mucosa. The methods of the present invention may also be used exclusive of, or as an adjunct to, hormone replacement therapy (HRT) or estrogen replacement therapy (ERT).

The present invention provides a method of stimulating cervical and vaginal secretions in a mammal, including a human, in need thereof by administering an amount of a compound of Formulas I, II, III, or IV or a pharmaceutically acceptable ester or salt thereof effective to increase said secretions.

UTP and its analogs are depicted in general Formula I:

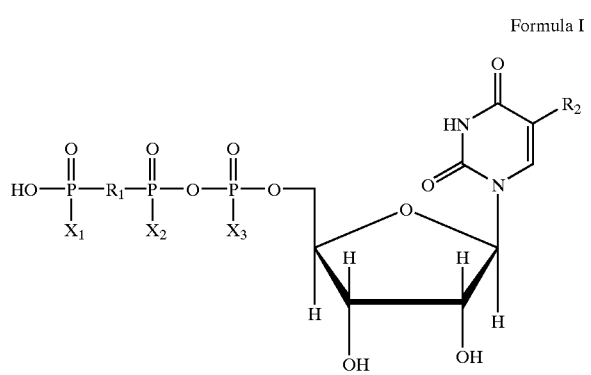

Formula I wherein:

wherein:

X is oxygen, methylene, difluoromethylene, imido;

n=0, 1, or 2;

m=0, 1, or 2;

n+m=0, 1, 2, 3, or 4; and

B and B' are each independently a purine residue or a pyrimidine residue linked through the 9- or 1-position, respectively;

Z=OH or $N_3$;

Z'=OH or $N_3$;

Y=H or OH;

Y'=H or OH;

provided that when Z is $N_3$, Y is H or when Z' is $N_3$, Y' is H.

The furanose sugar is preferably in the β-configuration.

The furanose sugar is most preferably in the β-D-configuration.

Preferred compounds of Formula II are the compounds of Formula IIa:

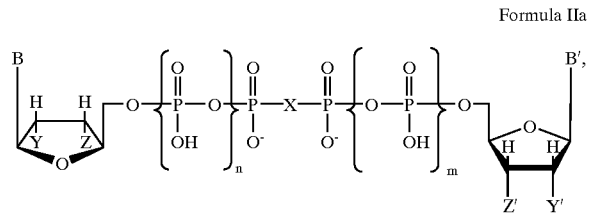

Formula IIa wherein:

X=O;

n+m=1 or 2;

Z, Z', Y, and Y'=OH;

B and B' are defined in Formulas IIc and IId;

X=O;

n+m=3 or 4;

Z, Z', Y, and Y'=OH;
B=uracil;
B' is defined in Formulas IIc and IId; or
X=O;
n+m=1 or 2;
Z, Y, and Y'=OH;
Z'=H;
B=uracil;
B' is defined in Formulas IIc and IId; or
n+m=0, 1, or 2;
Z and Y=OH;
Z'=$N_3$;
Y'=H;
B=uracil;
B'=thymine; or
X=O;
n+m=0, 1, or 2;
Z and Z'=$N_3$;
Y and Y'=H;
B and B'=thymine; or
X=$CH_2$, $CF_2$, or NH;
n and m=1;
Z, Z', Y, and Y'=OH;
B and B' are defined in Formulas IIc and IId.
Another preferred group of the compounds of Formula II are the compounds of Formula IIb or the pharmaceutically acceptable salts thereof:

Formula IIb

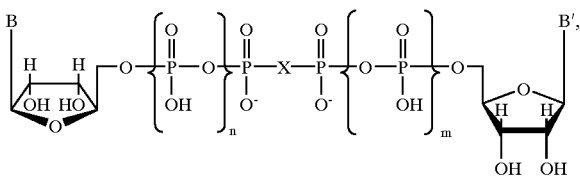

wherein:

X is oxygen, methylene, difluoromethylene, or imido;

n=0 or 1;

m=0 or 1;

n+m=0, 1, or 2; and

B and B' are each independently a purine residue, as in Formula IIc, or a pyrimidine residue, as in Formula IId, linked through the 9- or 1-position, respectively. In the instance where B and B' are uracil, attached at N-1 position to the ribosyl moiety, then the total of m+n may equal 3 or 4 when X is oxygen. The ribosyl moieties are in the D-configuration, as shown, but may be L-, or D- and L-. The D-configuration is preferred.

Formula IIc

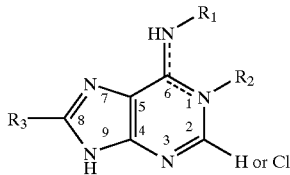

The substituted derivatives of adenine include adenine 1-oxide; 1,N6-(4- or 5-substituted etheno) adenine; 6-substituted adenine; or 8-substituted aminoadenine, where $R_1$ of the 6-HN$R_1$ group and $R_3$ are chosen from among: arylalkyl($C_{1-6}$) groups with the aryl moiety optionally functionalized as described below; alkyl; and alkyl groups with functional groups therein, such as: ([6-aminohexyl] carbamoylmethyl)-, and ω-acylated-amino(hydroxy, thiol and carboxy) derivatives where the acyl group is chosen from among, but not limited to, acetyl, trifluroroacetyl, benzoyl, substituted-benzoyl, etc., or the carboxylic moiety is present as its ester or amide derivative, for example, the ethyl or methyl ester or its methyl, ethyl or benzamido derivative. The ω-amino(hydroxy, thiol) moiety may be alkylated with a $C_{1-4}$ alkyl group.

Likewise, B or B' or both in Formula IIb may be a pyrimidine with the general formula of Formula IId, linked through the 1-position:

Formula IId

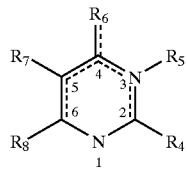

wherein:

$R_4$ is hydroxy, mercapto, amino, cyano, aralkoxy, $C_{1-6}$ alkoxy, $C_{1-6}$ alkylamino, and dialkylamino, the alkyl groups optionally linked to form a heterocycle;

$R_5$ is hydrogen, acyl, $C_{1-6}$ alkyl, aroyl, $C_{1-5}$ alkanoyl, benzoyl, or sulphonate;

$R_6$ is hydroxy, mercapto, alkoxy, aralkoxy, $C_{1-6}$-alkylthio, $C_{1-5}$ disubstituted amino, triazolyl, alkylamino, or dialkylamino, where the alkyl groups are optionally linked to form a heterocycle or linked to N-3 to form an optionally substituted ring;

$R_7$ is hydrogen, hydroxy, cyano, nitro, alkenyl, with the alkenyl moiety optionally linked through oxygen to form a ring optionally substituted on the carbon adjacent to the oxygen with alkyl or aryl groups, substituted alkynyl or hydrogen where $R_8$ is amino or substituted amino and halogen, alkyl, substituted alkyl, perhalomethyl (e.g., $CF_3$), $C_{2-6}$ alkyl, $C_{2-3}$ alkenyl, or substituted ethenyl (e.g., allylamino, bromvinyl and ethyl propenoate, or propenoic acid), $C_{2-3}$ alkynyl or 1=substituted alkynyl when $R_6$ is other than amino or substituted amino and together $R_5$–$R_6$ may form a 5- or 6-membered saturated or unsaturated ring bonded through N or O at $R_6$, such a ring may contain substituents that themselves contain functionalities;

$R_8$ is hydrogen, alkoxy, arylalkoxy, alkylthio, arylalkylthio, carboxamidomethyl, carboxymethyl, methoxy, methylthio, phenoxy, or phenylthio.

In the general structure of Formula IId above, the dotted lines in the 2- to 6-positions are intended to indicate the presence of single or double bonds in these positions; the relative positions of the double or single bonds being determined by whether the $R_4$, $R_6$, and $R_7$ substituents are capable of keto-enol tautomerism.

In the general structures of Formula IIc and IId above, the acyl groups advantageously comprise alkanoyl or aroyl groups. The alkyl groups advantageously contain 1 to 8 carbon atoms, particularly 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above mentioned alkenyl and alkynyl groups advantageously contain 2 to 8 carbon atoms, particularly 2 to 6 carbon atoms, e.g., ethenyl or ethynyl, optionally substituted by one or more appropriate substituents as described below. Appropriate substituents on the above-mentioned alkyl, alkenyl, alkynyl, and aryl groups are advantageously selected from halogen, hydroxy, $C_{1-4}$ alkoxy, $C_{1-4}$ alkyl, $C_{6-12}$ arylalkoxy, carboxy, cyano, nitro, sulfonamido, sulfonate, phosphate, sulfonic, amino, and substituted amino wherein the amino is singly or doubly substituted by a $C_{1-4}$ alkyl, and when doubly substituted, the alkyl groups optionally being linked to form a heterocycle.

For purposes of further clarifying the foregoing descriptions of Formulae IIc and IId, the descriptions can be simplified to the following:

$R_2$ is O or is absent; or $R_1$ and $R_2$ taken together may form optionally substituted 5-membered fused imidazole ring; or $R_1$ of the 6-$HNR_1$ group or $R_3$ of the 8-$HNR_3$ group is chosen from the group consisting of:
  (a) arylalkyl ($C_{1-6}$) groups with the aryl moiety optionally substituted,
  (b) alkyl,
  (c) ([6-aminohexyl]carbamoylmethyl),
  (d) ω-amino alkyl ($C_{2-10}$),
  (e) ω-hydroxy alkyl ($C_{2-10}$),
  (f) ω-thiol alkyl ($C_{2-10}$),
  (g) ω-carboxy alkyl ($C_{2-10}$),
  (h) the ω-acylated derivatives of (b), (c) or (d) wherein the acyl group is either acetyl, trifluroacetyl, benzoyl, or substituted-benzoyl alkyl($C_{2-10}$), and
  (i) ω-carboxy alkyl ($C_{2-10}$) as in (e) above wherein the carboxylic moiety is an ester or an amide;

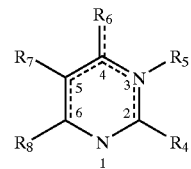

Formula IId wherein:

$R_4$ is hydroxy, mercapto, amino, cyano, aralkoxy, $C_{1-6}$ alkylthio, $C_{1-6}$ alkoxy, $C_{1-6}$ alkylamino or dialkylamino, wherein the alkyl groups of said dialkylamino are optionally linked to form a heterocycle;

$R_5$ is hydrogen, acyl, $C_{1-6}$ alkyl, aroyl, $C_{1-5}$ alkanoyl, benzoyl, or sulphonate;

$R_6$ is hydroxy, mercapto, alkoxy, aralkoxy, $C_{1-6}$-alkylthio, $C_{1-5}$ disubstituted amino, triazolyl, alkylamino or dialkylamino, wherein the alkyl groups of said dialkylamino are optionally linked to form a heterocycle or linked to $N^3$ to form an optionally substituted ring;

$R_5$–$R_6$ together forms a 5 or 6-membered saturated or unsaturated ring bonded through N or O at $R_6$, wherein said ring is optionally substituted;

$R_7$ is selected from the group consisting of:
  (a) hydrogen,
  (b) hydroxy,
  (c) cyano,
  (d) nitro,
  (e) alkenyl, wherein the alkenyl moiety is optionally linked through oxygen to form a ring optionally substituted with alkyl or aryl groups on the carbon adjacent to the oxygen,
  (f) substituted alkynyl
  (g) halogen,
  (h) alkyl,
  (i) substituted alkyl,
  (j) perhalomethyl,
  (k) $C_{2-6}$ alkyl,
  (l) $C_{2-3}$ alkenyl,
  (m) substituted ethenyl,
  (n) $C_{2-3}$ alkynyl and
  (o) substituted alkynyl when $R_6$ is other than amino or substituted amino;

$R_8$ is selected from the group consisting of:
  (a) hydrogen,
  (b) alkoxy,
  (c) arylalkoxy,
  (d) alkylthio,
  (e) arylalkylthio,
  (f) carboxamidomethyl,
  (g) carboxymethyl,
  (h) methoxy,
  (i) methylthio,
  (j) phenoxy and
  (k) phenylthio.

CTP and its analogs are depicted by general Formula III:

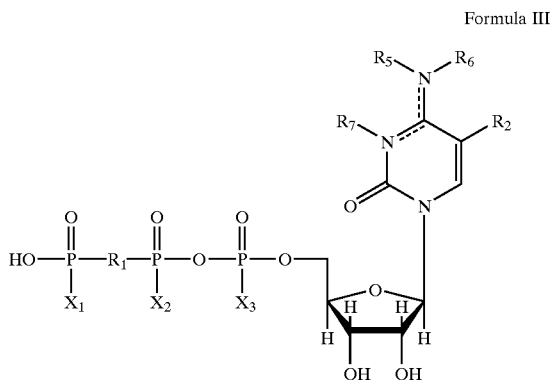

Formula III wherein:
$R_1$, $X_1$, $X_2$ and $X_3$ are defined as in Formula I;
$R_5$ and $R_6$ are H while $R_7$ is nothing and there is a double bond between N-3 and C-4 (cytosine), or
$R_5$, $R_6$ and $R_7$ taken together are —CH=CH—, forming a ring from N-3 to N-4 with a double bond between N-4 and C-4 (3,N4-ethenocytosine) optionally substituted at the 4- or 5-position of the etheno ring.

ATP and its analogs are depicted by general Formula IV:

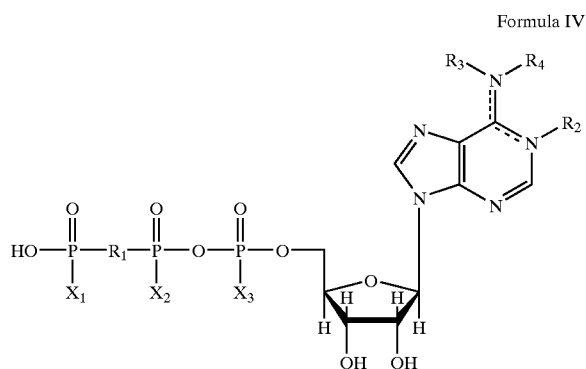

Formula IV wherein:
$R_1$, $X_1$, $X_2$, and $X_3$ are defined as in Formula I;
$R_3$ and $R_4$ are H while $R_2$ is nothing and there is a double bond between N-1 and C-6 (adenine), or
$R_3$ and $R_4$ are H while $R_2$ is O and there is a double bond between N-1 and C-6 (adenine 1-oxide), or
$R_3$, $R_4$, and $R_2$ taken together are —CH=CH—, forming a ring from N-6 to N-1 with a double bond between N-6 and C-6 (1,N6-ethenoadenine).

For simplicity, Formulas I, II, III, and IV herein illustrate the active compounds in the naturally occurring D-configuration, but the present invention also encompasses compounds in the L-configuration, and mixtures of compounds in the D-and L-configurations, unless otherwise specified. The naturally occurring D-configuration is preferred.

The compounds of the invention may be present in the form of their pharmaceutically acceptable salts, such as, but not limited to, an alkali metal salt such as sodium or potassium; an alkaline earth metal salt such as manganese, magnesium, or calcium; or an ammonium or tetraalkyl ammonium salt, i.e., $NX_4^+$ (wherein X is $C_{1-4}$). Pharmaceutically acceptable salts are salts that retain the desired biological activity of the parent compound and do not impart undesired toxicological effects. The compounds of the invention may also be present in the form of prodrugs, typically comprising esters or amide moieties on the heterocyclic and furanosyl hydroxyls of the compound.

Another aspect of the present invention is a method of treating a mammal with vaginal dryness arising from, but not limited to, menopause, childbirth, breastfeeding, chemotherapy or radiotherapy, diabetes mellitus, Sjögren's syndrome, Ehlers-Danlos syndrome, systemic sclerosis and other systemic autoimmune diseases, hysterectomy, urogenital surgery, psychosomatic disorders, anxiety, psychosexual problems, and pharmacological drug-related side effects.

It is also contemplated that the method of the present invention can be used to increase vaginal moisture and lubrication in healthy women for the purpose of facilitating sexual intercourse. It is further contemplated that the method of the present invention would be particularly useful for a woman who wished to accommodate a sexual partner who is undergoing treatment with Viagra® or other such drugs used for the treatment of erectile dysfunction.

The present invention further provides pharmaceutical compositions comprising a dosage form containing either $P2Y_2$ and/or $P2Y_4$ purinergic receptor agonists selected from the group consisting of general Formula I, i.e., uridine 5'-triphosphate [UTP] and its analogs, general Formula II, i.e., $P^1,P^4$-di(uridine-5') tetraphosphate [$U_2P_4$] and its analogs, general Formula III, i.e., cytidine 5'-triphosphate [CTP] and its analogs, and general Formula IV, i.e., adenosine 5'-triphosphate [ATP] and its analogs.

The compounds disclosed herein may be administered to the cervical and/or vaginal mucosa of a patient by any suitable means, but are preferably administered by a solution, gel, suspension, cream, foam, pessary, or tablet containing the active compound. Alternatively, the active compounds may by administered by continuous release from a vaginal ring (Stumpf, P., *Obstet. Gynecol.* 75:9S (1990)) or an intrauterine device (Andersson, K., et al., *Obstet. Gynecol.* 79:963 (1992)).

The topical solution, gel, jelly, ointment, cream, foam, pessary, or tablet contain the active compound in a physiologically compatible vehicle, as those skilled in the art of gynecological topical delivery system development can select using conventional criteria.

Solutions formulated for administration to the vagina are usually referred to as irrigations. These are sterile solutions, prepared in a manner typical of sterile injections that are intended for prepared as a single use sterile solution.

Gels or jellies may be produced using a suitable gelling agent including, but not limited to, gelatin, tragacanth, or a cellulose derivative and may include lycerol as a humectant, emollient, and preservative.

Ointments are semi-solid preparations that consist of the active ingredient ncorporated into a fatty, waxy, or synthetic base.

Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Pessaries are solid unit-dose forms suitably shaped for insertion into the vagina and may either be composed of a base that melts at body temperature or which dissolves when in contact with mucous secretions. Examples of suitable bases include, but are not limited to, theobroma oil, synthetic fat bases (e.g. Witepsol), polyethylene glycols (macrogols), and glycerol suppository basis.

Vaginal tablets are composed of the active ingredient contained within a solid dosage form base which may include, but not be limited to, excipients such as lactose, microcrystalline cellulose, corn starch, magnesium stearate, silicon dioxide, and hydroxypropyl methylcellulose.

In addition to the topical method of administration described above, there are various methods of administering the compounds of the present invention systemically. One such means would involve an aerosol suspension of respirable particles comprised of the active compound, which the subject inhales. The active compound would be absorbed into the bloodstream via the lungs and contact the cervical and/or vaginal tissues in a pharmaceutically effective amount. The respirable particles may be liquid or solid, with a particle size sufficiently small to pass through the mouth and larynx upon inhalation; in general, particles ranging from about 1 to 10 microns, but more preferably 1–5 microns, in size are considered respirable.

Another means of systemically administering the active compounds to the cervical and vaginal tissues of the subject would involve administering a liquid/liquid suspension in the form of nasal drops of a liquid formulation, or a nasal spray of respirable particles which the subject inhales. Liquid pharmaceutical compositions of the active compound for producing a nasal spray or nasal drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formulas I, II, III, or IV are in the form of tablets, lozenges, aqueous or oily suspensions, dispersible powders or granules, emulsion, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide pharmaceutically elegant and palatable preparations. Tablets contain the active ingredient in admixture with nontoxic pharmaceutically acceptable excipients which are suitable for the manufacture of tablets. These excipients may be, for example, inert diluents, such as calcium carbonate, sodium carbonate, lactose, calcium phosphate, or sodium phosphate; granulating and disintegrating agents, for example, corn starch or alginic acid; binding agents, for example, starch, gelatin, or acacia; and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example, peanut oil, liquid paraffin, or olive oil.

Additional means of systemic administration of the active compound to the cervical and vaginal tissues of the subject would involve a suppository form of the active compound, such that a therapeutically effective amount of the compound reaches the cervical and vaginal tissues via systemic absorption and circulation.

The quantity of the active compound included in the pharmaceutical composition is an amount sufficient to achieve concentrations of the active compound on the cervical and/or vaginal mucosa of the subject of from about $10^{-7}$ to about $10^{-1}$ Moles/liter, and more preferably from about $10^{-6}$ to about $10^{-1}$ Moles/liter.

Depending on the solubility of the particular formulation of active compound administered, the daily dose to promote cervical and/or vaginal mucin production and/or hydration may be divided among one or several unit dose administrations. The total daily dose for UTP (for example) may range from 1 to 1000 milligrams, depending upon the age and state of the subject, given at a regimen of up to four times per day or on an as needed basis to address acute exacerbations.

Some compounds of Formulas I, II, III, and IV can be made by methods which are well known to those skilled in the art and in accordance with known procedures (Zamecnik, P., et al., *Proc. Natl. Acad. Sci. USA* 89:2370–2373 (1992); Ng, K., et al., *Nucleic Acids Res.* 15:3572–3580 (1977); Jacobus, K. M., et al., U.S. Pat. No. 5,789,391 and Pendergast, W., et al., International Patent Application WO98/34942)); some are commercially available, for example, from Sigma Chemical Company, PO Box 14508, St. Louis, Mo. 63178. The synthetic methods of U.S. Pat. No. 5,789,391 and International Patent Application WO98/34942 are incorporated herein by reference.

EXAMPLES

Example 1

In Vitro Short Circuit ($I_{SC}$) Measurements

The compound UTP is a potent agonist of $P2Y_2$ and/or $P2Y_4$ purinergic receptors in cervical and vaginal tissue preparations by evaluation in vitro by administering UTP to the tissue culture sufficient to achieve concentrations of UTP on the mucosa of from about $10^{-7}$ to about $10^{-1}$ moles/liter. (Rojanasakul, Y., et al., *Pharm. Res.* 9:1029–34 (1992); Bechgaard, E., et al., *Int. J. Pharm.* 106:237–242 (1994); Gipson, I., et al., *Biol. Reprod.* 56:999–1011, (1997)). Specifically, ovariectomized female white albino New Zealand rabbits are sacrificed and vaginal tissue is removed. The tissue is mounted on a supporting ring and clamped in an Using chamber. $I_{SC}$ is measured as flowing from the epithelial side to the serosal side of the tissue. Approximately half of this current corresponds to chloride movement through the membrane and hence, this is an accurate measure of the corresponding fluid movement.

Example 2

In Vivo Study in Rabbits

The compounds of the invention are evaluated in vivo by administrating UTP, or any of the other $P2Y_2$ and/or $P2Y_4$ agonists of the present invention to an animal in an amount sufficient to achieve concentrations of $P2Y_2$ and/or $P2Y_4$ agonist on the cervical and/or vaginal mucosa of the animal of from about $10^{-7}$ to about $10^{-1}$ moles/liter (Richardson, J., et al., *Int. J. Pharm.* 56:29–35 (1989)). Specifically, ovariectomized female white albino New Zealand rabbits are dosed with a $P2Y_2$ and/or $P2Y_4$ agonist such as any of the compounds of the present invention. A vaginal smear is then obtained with a cotton swab. The sample is appropriately prepared, an ELISA or a calorimetric dot blot method is run on the sample, and the relative amounts of representative cervical mucins are determined as compared to non-ovariectomized controls. (Gipson, I. et al., *Biol. Reprod.* 56:999–1011 (1997)).

Example 3

In Vivo Study Using Ovarectomized Cynologous Monkeys

The compounds of the present invention are evaluated in vivo with an animal model of vaginal dryness as follows. Ovariectomized cynomolgus monkeys are examined before treatment and graded subjectively using a fabinal atrophy index. The animals were then dosed intravaginally with 100 to 300 μl mist containing $10^{-2}$ to 1 moles/liter $P2Y_2$ and/or $P2Y_4$ agonist, such as any of the compounds of the present invention. After 10, 20, 30, 60 and 90 minutes the animals are subjected to a gynecological exam and graded by qualified medical professions with the vaginal atrophy index on a scale of 1 to 5, including a measurement of fluid pH. (Hubbard, G. et al., *Lab Animal Sci.* 47, 36–39, (1997)).

What is claimed is:

1. A method of treating a mammal with vulvar pain by administering an effective vulvar pain treatment amount of a compound of Formula II:

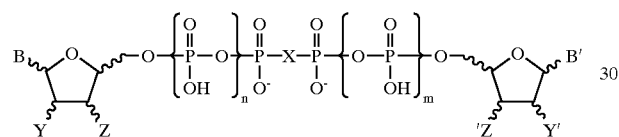

Formula II wherein:
X is oxygen, methylene, difluoromethylene, imido;
n=0, 1, or 2;
m=0, 1, or 2;
n+m=0, 1, 2, 3, or 4; and
B and B' are each independently a purine residue or a pyrimidine residue linked through the 9- or 1-position, respectively;
Z=OH or $N_3$;
Z'=OH or $N_3$;
Y=H or OH;
Y'=H or OH;
provided that when Z is $N_3$, Y is H and when Z' is $N_3$, Y' is H.

2. The method of claim 1 wherein the compounds of Formula II are those of Formula IIa:

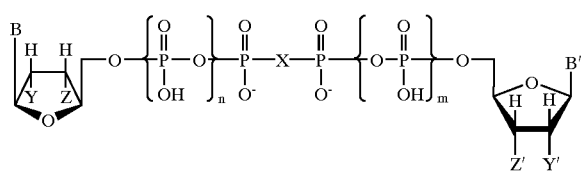

Formula IIa wherein:
X=O;
n+m=1 or 2;
Z, Z', Y, and Y'=OH;

B and B' are defined in Formulas IIc and IId, or
X=O;
n+m=3 or 4;
Z, Z', Y, and Y'=OH;
B=uracil;
B' is defined in Formulas IIc and IId; or
X=O;
n+m=1 or 2;
Z, Y, and Y'=OH;
Z'=H;
B=uracil;
B' is defined in Formulas IIc and IId; or
X=O;
n+m=0, 1, or 2;
Z and Y=OH;
Z'=$N_3$;
Y'=H;
B=uracil;
B'=thymine; or
X=O;
n+m=0, 1, or 2;
Z and Z'=$N_3$;
Y and Y'=H;
B and B'=thymine; or
X=$CH_2$, $CF_2$, or NH;
n and m=1;
Z, Z', Y, and Y'=OH;
B and B' are defined in Formulas IIc and IId:

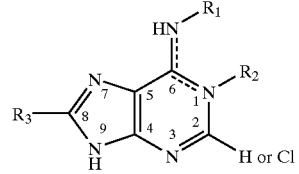

Formula IIc

Wherein $R_1$ of the 6-$HNR_1$ group and $R_3$ are chosen from the group consisting of:
(a) arylalkyl ($C_{1-6}$) groups with the aryl moiety optionally substituted,
(b) alkyl,
(c) ([6-aminohexyl]carbamoylmethyl),
(d) ω-amino alkyl ($C_{2-10}$),
(e) ω-hydroxy alkyl ($C_{2-10}$),
(f) ω-thiol alkyl ($C_{2-10}$),
(g) ω-carboxy alkyl ($C_{2-10}$),
(h) the ω-acylated derivatives of (b), (c) or (d) wherein the acyl group is either acetyl, trifluroacetyl, benzoyl, or substituted-benzoyl alkyl($C_{2-10}$),
(i) ω-carboxy alkyl ($C_{2-10}$) as in (e) above wherein the carboxylic moiety is an ester or an amide, and
(j) hydrogen;

$R_2$ is O or is absent; or $R_1$ and $R_2$ taken together may form optionally substituted 5-membered fused imidazole ring;

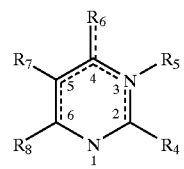

Formula IId wherein:

$R_4$ is hydroxy, mercapto, amino, cyano, aralkoxy, $C_{1-6}$ alkylthio, $C_{1-6}$ alkoxy, $C_{1-6}$ alkylamino or dialkylamino, wherein the alkyl groups of said dialkylamino are optionally linked to form a heterocycle;

$R_5$ is hydrogen, acyl, $C_{1-6}$ alkyl, aroyl, $C_{1-5}$ alkanoyl, benzoyl, or sulphonate;

$R_6$ is hydroxy, mercapto, alkoxy, aralkoxy, $C_{1-6}$-alkylthio, $C_{1-5}$ disubstituted amino, triazolyl, alkylamino or dialkylarnino, wherein the alkyl groups of said dialkylamino are optionally linked to form a heterocycle or linked to $N^3$ to form an optionally substituted ring; or $R_5$–$R_6$ together forms a 5 or 6-membered saturated or unsaturated ring bonded through N or O at $R_6$, wherein said ring is optionally substituted;

$R_7$ is selected from the group consisting of:
(a) hydrogen,
(b) hydroxy,
(c) cyano,
(d) nitro,
(e) alkenyl, wherein the alkenyl moiety is optionally linked through oxygen to form a ring optionally substituted with alkyl or aryl groups on the carbon adjacent to the oxygen,
(f) substituted alkynyl
(g) halogen,
(h) alkyl,
(i) substituted alkyl,
(j) perhalomethyl,
(k) $C_{2-6}$ alkyl,
(l) $C_{2-3}$ alkenyl,
(m) substituted ethenyl,
(n) $C_{2-3}$ alkynyl and
(o) substituted alkynyl when $R_6$ is other than amino or substituted amino;

$R_8$ is selected from the group consisting of:
(a) hydrogen,
(b) alkoxy,
(c) arylalkoxy,
(d) alkylthio,
(e) arylalkylthio,
(f) carboxamidomethyl,
(g) carboxymethyl,
(h) methoxy,
(i) methylthio,
(j) phenoxy and
(k) phenylthio.

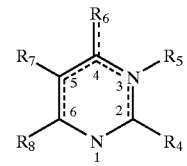

Formula IId

3. The method of claim 1 wherein the compounds of Formula II are those of Formula IIb:

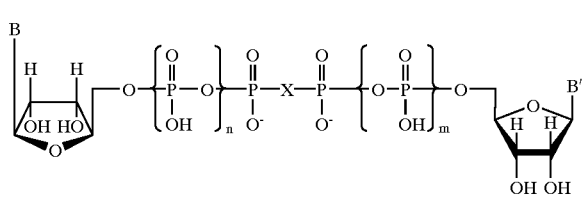

Formula IIb wherein:

X is oxygen, methylene, difluoromethylene, or imido;

n=0 or 1;

m=0 or 1;

n+m=0, 1, or 2; and

B and B' are each independently a purine residue, as in Formula IIc as described in claim 2, or a pyrimidine residue, as in Formula IId as described in claim 2, linked through the 9- or 1-position, respectively; provided that when B and B' are uracil, attached at N-1 position to the ribosyl moiety, then the total of m+n equals 3 or 4 when X is oxygen.

4. The method of claim 1 wherein the furanose sugar of Formula II is in the β-D-configuration.

5. A pharmaceutical composition comprising a compound of Formula as described in claim 1 together with a pharmaceutically acceptable carrier therefor in the form of a liquid or gel suspension.

6. The method of claim 1 wherein the amount of compound of Formula II, administered to the mammal is sufficient to achieve a concentration on the cervical and/or vaginal mucosa of from about $10^{-7}$ moles/liter to about $10^{-1}$ moles/liter.

7. The method of claim 1 wherein the amount of compound of Formula II, administered to the mammal is sufficient to achieve a daily dose of between 1 to 1000 milligrams.

8. A method of treating a mammal with vulvar pain by administrating an effective vulvar pain treatment amount of a compound of $P^1$, $P^4$-di(uridine-5')tetraphosphate.

* * * * *

UNITED STATES PATENT AND TRADEMARK OFFICE
CERTIFICATE OF CORRECTION

PATENT NO. : 6,462,028 B2 Page 1 of 1
APPLICATION NO. : 09/199912
DATED : October 8, 2002
INVENTOR(S) : William Pendergast et al.

It is certified that error appears in the above-identified patent and that said Letters Patent is hereby corrected as shown below:

Column 10, line 51, change "ncorporated" to --incorporated--.

Column 13, line 7, in the title of Example 3, change "Ovarectomized" to

--Ovariectomized--.

Column 13, line 14, in Example 3, change "were" to --are--.

In the Claims:

Column 13, line 50, Claim 2, delete "go".

Signed and Sealed this

Twenty-seventh Day of November, 2007

JON W. DUDAS
*Director of the United States Patent and Trademark Office*